United States Patent
Matsushita

[19]

[11] Patent Number: 5,885,264
[45] Date of Patent: Mar. 23, 1999

[54] DISPOSABLE TRAINING PANTS

[75] Inventor: Michiyo Matsushita, Ehime-ken, Japan

[73] Assignee: Uni-Charm Corporation, Ehime-ken, Japan

[21] Appl. No.: 887,050

[22] Filed: Jul. 2, 1997

[30] Foreign Application Priority Data

Jul. 2, 1996 [JP] Japan .................................. 8-172325

[51] Int. Cl.$^6$ .................................................. A61F 13/15
[52] U.S. Cl. ........................ 604/361; 604/364; 604/385.1
[58] Field of Search .............................. 604/385.1, 361, 604/364, 367, 378

[56] References Cited

U.S. PATENT DOCUMENTS

| | | | |
|---|---|---|---|
| 4,834,733 | 5/1989 | Huntoon et al. | 604/361 |
| 5,037,416 | 8/1991 | Allen et al. | 604/385.1 |
| 5,342,343 | 8/1994 | Kitaoka et al. | 604/385.2 |
| 5,425,726 | 6/1995 | Shimizu et al. | 604/385.1 |

FOREIGN PATENT DOCUMENTS

| | | |
|---|---|---|
| 4-5961 | 1/1992 | Japan . |
| 5-59601 | 3/1993 | Japan . |

*Primary Examiner*—John G. Weiss
*Assistant Examiner*—Dennis Ruhl
*Attorney, Agent, or Firm*—Lowe Hauptman Gopstein Gilman & Berner

[57] ABSTRACT

A disposable training pant 1 includes a liquid-permeable topsheet, a liquid-impermeable backsheet and an absorbent core disposed therebetween. The liquid-permeable tophseet includes an upper layer sheet and a lower layer sheet. The upper layer sheet is formed with a wetness telling area and the lower layer sheet intermittently bonded to the absorbent core 13 and containing fibrous material adapted to shrink by 10% or more longitudinally of the training pant as it is wetted and intermittently bonded to the absorbent core and thereby intensify a feeling of wetness given to the infant.

9 Claims, 3 Drawing Sheets

DISPOSABLE TRAINING PANTS

BACKGROUND OF THE INVENTION

This invention relates generally to disposable training pants and more particularly to such a pants that can be used when infants grow out of diapers and that include a wetness telling area.

Japanese Laid-Open Patent Application No. Hei4-5961 discloses a topsheet of a disposable training pant partially formed with a wetness telling area having a hydrophilicity. In a disposable training pant described in Japanese Laid-Open Patent Application No. Hei5-59601, the topsheet is provided at least over a middle area thereof with a moistness holding sheet partially bonded thereto and partially rising from the topsheet.

In disposable training pants or diapers comprising a liquid-permeable topsheet, a liquid-impermeable backsheet and a liquid-absorbent core extending between these two sheets, it is well known to keep the topsheet in close contact with the absorbent core by intermittently bonding these two components to each other so that a quantity of discharged body fluids may be transferred to the absorbent core as rapidly as possible. However, if the topsheet is bonded to the absorbent core in this manner in the disposable training pants or diaper as disclosed in the above-identified Applications, transfer of body fluids can be accelerated but only a small quantity of body fluids can stay in the wetness telling area or the moistness holding sheet and a feeling of wetness given to the infant by such area or sheet is correspondingly weakened.

SUMMARY OF THE INVENTION

In view of the problem as has been described above, it is a principal object of the invention to facilitate a quantity of body fluids to be held in a wetness telling area.

The object set forth above is achieved, according to the invention, by a disposable training pant comprising a liquid-permeable topsheet, a liquid-impermeable backsheet and a liquid-absorbent core extending therebetween which form a front waist region, a rear waist region and a crotch region extending therebetween, said topsheet being intermittently bonded to said absorbent core and bonded to said backsheet at portions of said topsheet and said backsheet extending outward beyond a peripheral edge of said absorbent core, on wherein:

said topsheet contains a fibrous material causing at least a longitudinal dimension of said crotch region to shrink by at least 10% as said topsheet is wetted so that said topsheet can shrink at least longitudinally of said crotch region and at least a shrinkable area of said topsheet can peel off upward from said absorbent core and wherein a predetermined area of said topsheet has a hydrophilicity higher than that in an area extending around said predetermined area and thereby defines a wetness telling area.

The invention allows the infant to perceive a wetness even if the training pant have slipped downward after it was worn, since the topsheet of the inventive disposable training pant shrinks longitudinally of the pant practically as soon as it is wetted with urine, thereupon peels off from the absorbent core and moves upward in close contact with the infant's skin. Once having peeled off from the absorbent core, the topsheet remains impregnated with the quantity of discharged urine for a long period and thereby intensifies a feeling of wetness given to the infant by the wetness telling area.

Other and further objects, features and advantages of the invention will appear more fully from the following description.

DESCRIPTION OF THE PREFERRED EMBODIMENT

Figure 1:
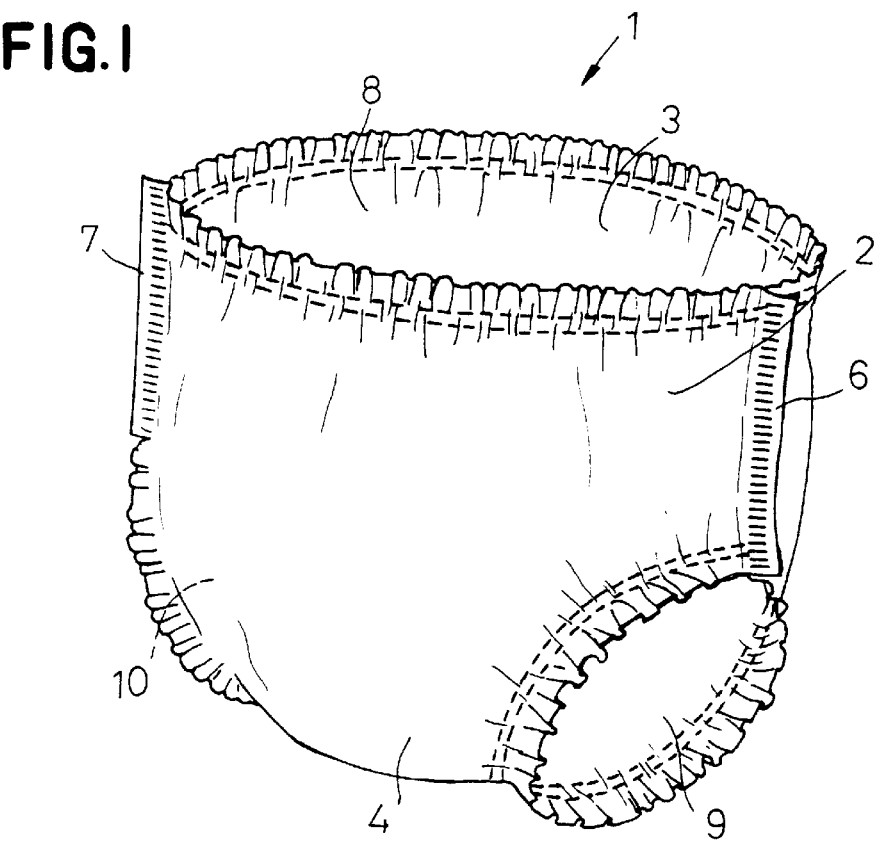
FIG. 1 is a perspective view showing a disposable training pant as an embodiment of the invention.

A disposable training pant 1 shown by FIG. 1 in a perspective view comprise a front waist region 2, a rear waist region 3 and a crotch region 4. The front and rear waist regions 2, 3 are bonded to each other along transversely opposite side edges 6, 7 thereof so as to form a waist-opening 8 and a pair of leg-openings 9, 10.

Figure 2:
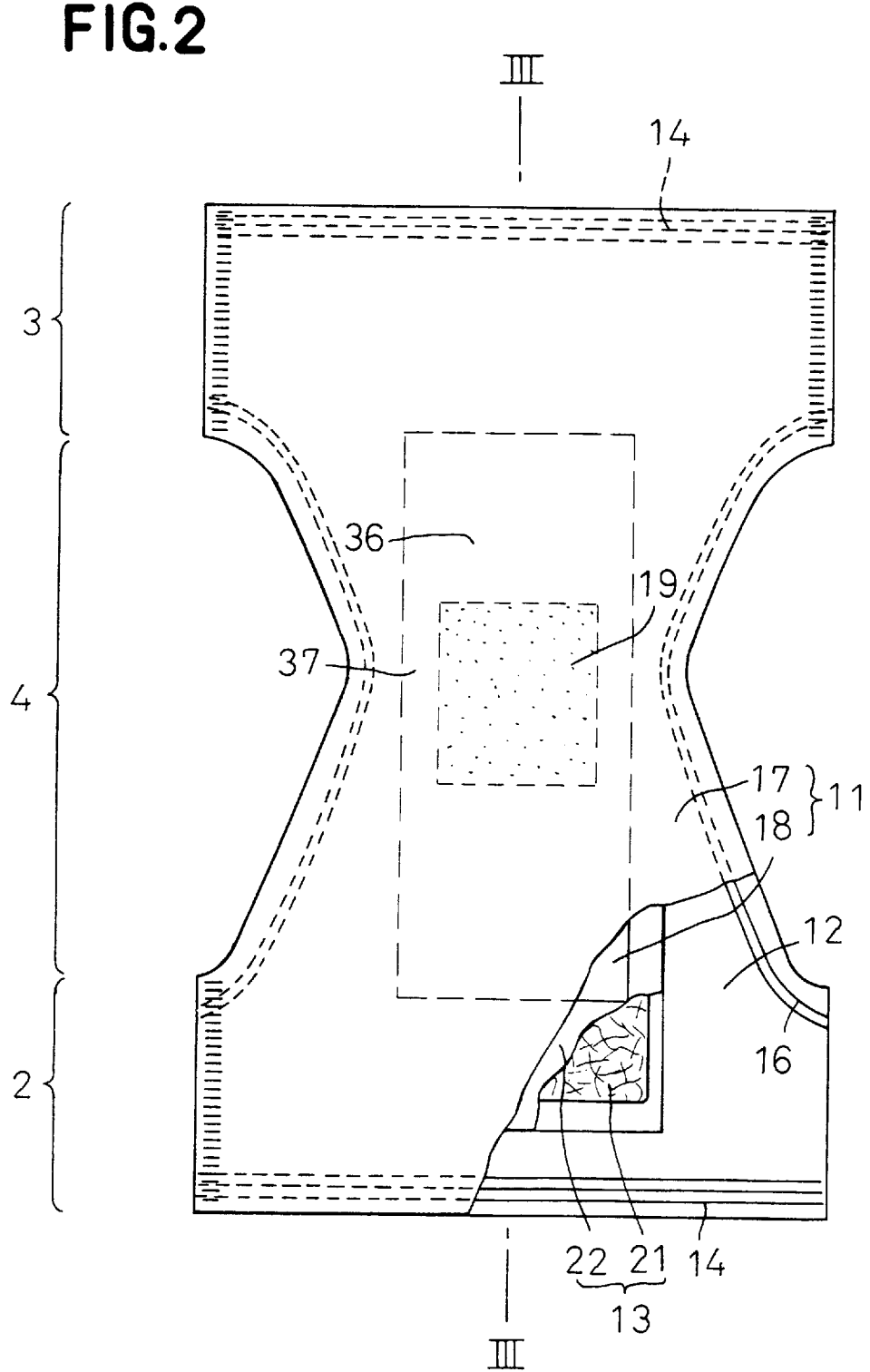
FIG. 2 is a plan view showing the training pant longitudinally unfolded, after transversely opposite side edges thereof have been peeled off from each other back and forth, as partially broken away.

FIG. 2 is a sectional view showing the training pant longitudinally unfolded after the front and rear waist regions 2, 3 have been separated from each other back and forth along the side edges 6, 7 as partially broken away. The training pant 1 comprises a liquid-permeable topsheet 11, a liquid-impermeable backsheet 12 and a liquid-absorbent core 13 extending between these two sheets 11, 12. The topsheet 11 and the backsheet 12 are bonded to each other at portions thereof extending outward beyond a peripheral edge of the absorbent core 13 with a plurality of elastic members 14 serving to fit the training pant 1 around the infant's waist and a plurality of elastic members 16 serving to fit the training pant 1 around the infant's legs being bonded in elastically stretched conditions to inner surface(s) of the topsheet 11 and/or the backsheet 12.

The topsheet 11 comprises an upper layer sheet 17 and a lower layer sheet 18. The upper layer sheet 17 defines the entire inner surface of the training pant 1 and the lower layer sheet 18 is in the form of a rectangular sheet which occupies a transversely middle zone of the training pant 1 and extends longitudinally thereof. As will be described later in reference with FIG. 3, the lower layer sheet 18 is bonded to a bottom surface of the upper layer sheet 17. The upper layer sheet 17 is formed by a liquid-permeable nonwoven fabric made of hydrophobic thermoplastic synthetic fibers and locally treated so as to become hydrophilic and thereby to define a wetness-telling area 19 (indicated by a dotted area in FIG. 2). The lower layer sheet 18 is made of a liquid-permeable nonwoven fabric adapted to shrink longitudinally by 10% or more when it is wetted. As a well known example of such nonwoven fabric, Japanese Patent Publication No. Hei6-102068 discloses a nonwoven fabric of polyvinyl alcohol fibers obtained by a spinning aqueous solution of polyvinyl alcohol having a polymerization degree of 1200~3000 and a sponification degree of 98.0 or higher.

As the backsheet 12, a film of thermoplastic synthetic resin is used.

The absorbent core 13 comprises a liquid-absorbent panel 21 and upper and lower liquid-absorbent sheets 22 such as hydrophilic tissue papers of wood pulp fibers having a high absorptivity as well as a high diffusibility and covering the absorbent panel 21. The absorbent panel 21 contains fluff pulp fibers of 50% by weight or higher, water-absorptive polymer particles of less than 50% by weight and thermoplastic synthetic fibers of less than 20% by weight.

Figure 3:
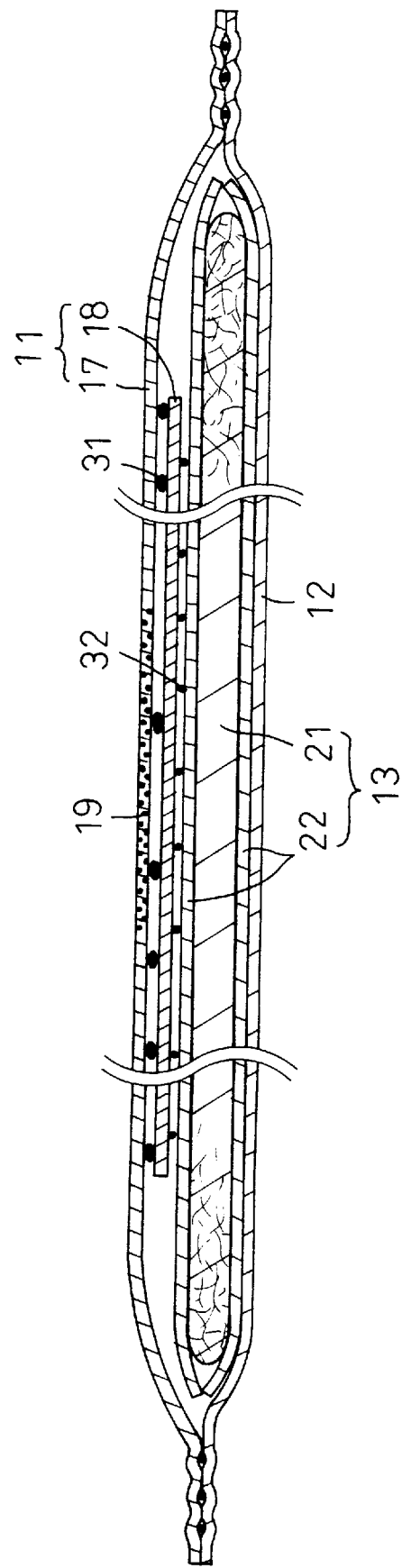
FIG. 3 is a sectional view taken along line III—III in FIG. 2.

FIG. 3 is a sectional view taken along line III—III (center line) in FIG. 2. Regarding the topsheet 11, the upper layer sheet 17 is bonded to the lower layer sheet 18 by means of intermittently applied first hot melt adhesives 31, on one hand, and the lower layer sheet 18 is bonded to the upper liquid-absorbent sheet 22 by means of intermittently applied second hot melt adhesives 32, on the other hand. The first adhesives 31 should be principally urine-insoluble but the second adhesives 32 may be either urine-soluble or urine-insoluble as circumstances require.

When urine is discharged in the training pants 1 constructed as has been described above, a quantity of discharged urine rapidly moves into the absorbent core 13 because the topsheet 1 remains in close contact with the absorbent core 13 for a while. As a time elapses, the lower layer sheet 18 of the topsheet 11 begins to shrink and the second adhesives 32 begin to be solved in urine so far as the second adhesives 32 is of water or urine-soluble type. Consequently, an adhesive force tending to maintain the lower layer sheet 18 and the liquid-absorbent sheet 22 bonded to each other begins to weaken. As the shrinkage progresses and adhesive force further weakens, the lower layer sheet 18 is peeled off from the upper liquid-absorbent sheet 22 and becomes free to shrink. When the second adhesives 32 are of water-urine-insoluble type, the quantity of urine permeates the upper liquid-absorbent sheet 22 also in the proximity of interfaces between the second adhesives 32 and the upper liquid-absorbent sheet 22. Eventually, the wood pulp fibers of the upper liquid-absorbent sheet 22 at the interfaces are swelled by the quantity of urine and this urine permeates the interfaces until the second adhesives 32 come off from the upper liquid-absorbent sheet 22. As a result, the lower layer sheet 18 is separated from the upper liquid-absorbent sheet 22 and become free to shrink.

Figure 4:
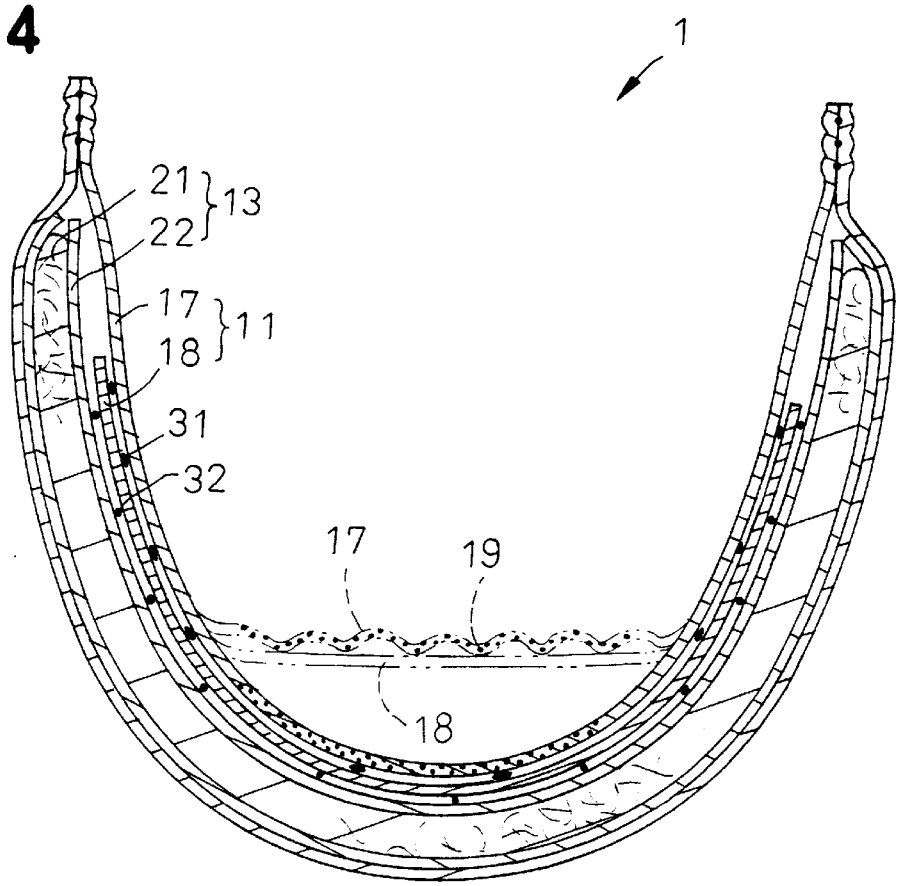
FIG. 4 is a sectional end view taken along a longitudinal center line of the training pant as put on the infant.

FIG. 4 is a sectional view taken along the longitudinal center line of the training pant 1 as worn showing a behavior of the topsheet 11 before and after discharge of urine. With the training pant 1 curved as shown on the infant's body, the quantity of urine discharged makes the lower layer sheet 18 of the topsheet 11 free to shrink and consequently peels the lower layer sheet 18 upward off from the absorbent core 13 as indicated by imaginary lines, allowing the lower sheet 18 to come in close contact with the infant's skin. Since the upper layer sheet 17 is integral with the lower layer sheet 18, the upper layer sheet 17 forms gathers and moves upward together with the lower layer sheet 18 as the lower sheet 18 shrinks. A portion of the upper layer sheet 17 adapted to move upward is formed with the wetness telling area 19. Accordingly, the wetness telling area 19 is kept in contact with the infant's skin and is able to fulfill its desired function even if the training pant 1 somewhat has slipped down after the training pant 1 was worn. If discharge of urine is repeated after the topsheet 11 has been peeled off from the absorbent core 13, this quantity of urine discharged again will stay in and around the wetness telling area 19 for a long period without being readily absorbed by the absorbent core 13, giving the infant an intense feeling of wetness.

With the training pant 1 according to the invention, the lower layer sheet 18 in the embodiment shown may be replaced by a plurality of threads adapted to shrink when they are wetted. As a well known example of such threads, Japanese Patent Publication No. Hei6-102068 discloses threads made from polyvinyl alcohol. Such threads may be provided so as to extend not only longitudinally but also transversely of the training pant 1 to accelerate shrinkage as well as peeling off of the upper layer sheet 17 with respect to the absorbent core 13 occurring when the upper layer sheet 17 is wetted. To form the upper layer sheet 17 with the wetness telling area 19, the individual fibers of the wetness telling area 19 may be applied with a suitable agent or water-absorbent fibers may be mixed into the individual fibers of the wetness telling area 19 to make the wetness telling area substantially hydrophilic. Preferably, the lower layer sheet 18 is intermittently bonded to the upper liquid-absorbent sheet 22 in order that the lower layer sheet 18 can be free to shrink and an area over which these two sheets 18, 22 are bonded to each other is smaller in a region 37 (FIG. 2) extending outside the transversely opposite side edges than in a region 36 (FIG. 2) extending outside the longitudinally opposite ends of the wetness telling area 19. Outside said transversely opposite side edges of the wetness telling area 19, the lower layer sheet 18 and the upper liquid-absorbent sheet 22 may be substantially or completely free from being bonded to each other. Preferably, the lower layer sheet 18 is shrinkable by 10% or higher approximately 10 seconds after the lower layer sheet 18 begins to be wetted in order that the infant can perceive a wetness as soon as possible after discharge of urine has occurred and thereby an effect of training for the infant can be improved. A peel strength of the second adhesives 32 used to bond such lower layer sheet 18 to the upper liquid-absorbent sheet 22 is preferably selected in a range from 100 g/25 mm of width under its dry condition to 5 g/25 mm of width under its wetted condition. The peel strength under the wetted condition is measured after the topsheet 11 has been impregnated with 50% of a saturated moisture content and left as it is. As the second adhesives 32, it is preferred to employ a rubber hot melt adhesive containing a base material such as SBS, SIS, SEBS or SEPS and having a solidifying time less than 2 seconds. The upper and lower layers 17, 18 of the topsheet 11 may be bonded to each other by the well known heat-sealing technique instead of using the first adhesives 31.

The entire disclosure of Japanese Patent Application No. 8-172325 filed on Jul. 2, 1996 including specification, claims, drawings and abstract are incorporated herein by refernece in its entirety.

Having described the invention as related to the embodiment shown in the accompanying drawings, it is our intention that the invention be not limited by any of the details of description, unless otherwise specified, but rather be construed broadly within its spirit and scope as set out in the accompanying claims.

What is claimed is:

1. A disposable training pant comprising a liquid-permeable topsheet, a liquid-impermeable backsheet and a liquid-absorbent core extending therebetween which form a front waist region, a rear waist region and a crotch region extending therebetween said topsheet being intermittently bonded to said absorbent core and bonded to said backsheet at portions of said topsheet and said backsheet extending outward beyond a peripheral edge of said absorbent core, wherein:

said topsheet contains a fibrous material causing at least a longitudinal dimension of said crotch region to shrink by at least 10% as said topsheet is wetted so that said topsheet can shrink at least longitudinally of said crotch region and at least a shrinkable area of said topsheet can peel off upward from said absorbent core and wherein a predetermined area of said topsheet has a hydrophilicity higher than that in the area extending around said predetermined area and thereby defines a wetness telling area.

2. The disposable training pant according to claim 1, wherein said topsheet contains also a fibrous material adapted to shrink transversely of said crotch region as said topsheet is wetted.

3. The disposable training pant according to claim 1, wherein said fibrous material comprises a nonwoven fabric forming at least a part of lower side of said topsheet.

4. The disposable training pant according to claim 2, wherein said fibrous material comprises threads extending at least longitudinally of said crotch region and bonded to the lower side of said topsheet.

5. The disposable training pant according to claim 1, wherein said absorbent core comprises a liquid-absorbent panel containing fluffy pulp of 50–100% by weight and a liquid-absorbent sheet covering said absorbent panel and wherein said topsheet is bonded to said liquid-absorbent sheet by an adhesive agent.

6. The disposable training pant according to claim 1, wherein said topsheet is bonded to said absorbent core by a water-soluble adhesive agent and said adhesive agent is solved in urine as said topsheet is wetted whereupon said topsheet can peel off from said absorbent core.

7. The disposable training pant according to claim 1, wherein said topsheet comprises a liquid-permeable upper layer sheet and a hydrophilic lower layer sheet bonded at least to a part of lower side of said upper layer sheet.

8. The disposable training pant according to claim 7, wherein said lower layer sheet is bonded to said absorbent core by a water-soluble agent.

9. The disposable training pant according to claim 7, wherein said lower layer sheet comprises wood pulp fibers which are swelled in contact with urine, and said lower layer sheet is bonded to said absorbent core by a water-insoluble agent.

* * * * *